(12) United States Patent
Pufahl

(10) Patent No.: US 10,359,441 B2
(45) Date of Patent: Jul. 23, 2019

(54) REAGENT STATION FOR AN AUTOMATED ANALYSIS DEVICE

(71) Applicant: Siemens Healthcare Diagnostics Products GmbH, Marburg (DE)

(72) Inventor: Holger Pufahl, Liederbach (DE)

(73) Assignee: Siemens Healthcare Diagnostics Products GmbH, Marburg (DE)

( * ) Notice: Subject to any disclaimer, the term of this patent is extended or adjusted under 35 U.S.C. 154(b) by 8 days.

(21) Appl. No.: 14/076,748

(22) Filed: Nov. 11, 2013

(65) Prior Publication Data

US 2014/0141518 A1 May 22, 2014

(30) Foreign Application Priority Data

Nov. 12, 2012 (EP) ..................................... 12192158

(51) Int. Cl.
*G01N 35/02* (2006.01)
*G01N 35/04* (2006.01)
*G01N 35/00* (2006.01)

(52) U.S. Cl.
CPC ........... *G01N 35/025* (2013.01); *G01N 35/04* (2013.01); *G01N 35/00029* (2013.01); *G01N 2035/00752* (2013.01); *G01N 2035/00811* (2013.01); *G01N 2035/0443* (2013.01); *G01N 2035/0453* (2013.01); *G01N 2035/0465* (2013.01); *Y10T 436/114165* (2015.01)

(58) Field of Classification Search
CPC ....... G01N 35/025; G01N 2035/00752; G01N 2035/0465; G01N 35/00029
See application file for complete search history.

(56) References Cited

U.S. PATENT DOCUMENTS

| 4,456,037 A * | 6/1984 | Gocho ............... G01N 35/1004 134/21 |
| 7,360,984 B1 * | 4/2008 | Sugiyama et al. ......... 414/798.1 |
| 2004/0057872 A1 | 3/2004 | Shibuya et al. |
| 2005/0013735 A1 * | 1/2005 | Gebrian ............. G01N 35/1002 422/63 |
| 2005/0207938 A1 * | 9/2005 | Hanawa et al. ................ 422/64 |
| 2006/0159587 A1 * | 7/2006 | Fechtner .............. G01N 35/025 422/64 |

(Continued)

FOREIGN PATENT DOCUMENTS

| CN | 1576849 A | 2/2005 |
| CN | 2762135 Y | 3/2006 |

(Continued)

OTHER PUBLICATIONS

European Search Report and Written Opinion of European Patent Application No. 12192158.9 dated May 10, 2013.

(Continued)

*Primary Examiner* — Lyle Alexander
*Assistant Examiner* — Dwan A Gerido
(74) *Attorney, Agent, or Firm* — Dugan & Dugan, PC

(57) ABSTRACT

The invention relates to a reagent station (1) for an automated analysis device, comprising a first and a second reagent container storage (2, 10) and a transfer apparatus (20) which transfers reagent containers (16) between the first and the second reagent container storage (2, 10). Furthermore, the invention relates to a method for loading an automated analysis device with reagent containers.

19 Claims, 1 Drawing Sheet

(56) References Cited

U.S. PATENT DOCUMENTS

2009/0117620 A1* 5/2009 Fritchie ............... B01L 3/5085
                                                                                                 435/91.1
2012/0301359 A1* 11/2012 Kraemer ............... G01N 35/04
                                                                                                 422/64

FOREIGN PATENT DOCUMENTS

| | | | |
|---|---|---|---|
| CN | 1875280 | A | 12/2006 |
| CN | 101726616 | A | 6/2010 |
| CN | 102221626 | A | 10/2011 |
| CN | 102326087 | A | 1/2012 |
| CN | 102590539 | A | 7/2012 |
| CN | 102597785 | A | 7/2012 |
| CN | 202471737 | U | 10/2012 |
| EP | 2333563 | * | 6/2011 |
| EP | 2333563 | A1 | 6/2011 |
| JP | H07-140149 | | 6/1995 |
| JP | H08-201396 | | 8/1996 |
| JP | 2003-262642 | | 9/2003 |
| JP | 2004-045112 | | 2/2004 |
| JP | 2004-226253 | | 8/2004 |
| JP | 2005-037171 | | 2/2005 |
| JP | 2007-524082 | | 8/2007 |
| JP | 2008-096223 | | 4/2008 |
| JP | 2008-216173 | | 9/2008 |
| JP | 2008216173 | A | 9/2008 |
| JP | 2009-068992 | | 4/2009 |
| JP | 2012-021862 | | 2/2012 |
| JP | 2012-189611 | | 10/2012 |
| JP | WO2011093030 | | 5/2013 |

OTHER PUBLICATIONS

Chinese Search Report of Chinese Application No. 2013105569724 dated May 5, 2016.
Chinese Office Action and Search Report of Chinese Application No. 2013105569724 dated May 13, 2016.
European Search Report of European Application No. 12 192 158.9-1553 dated Sep. 8, 2017.

* cited by examiner

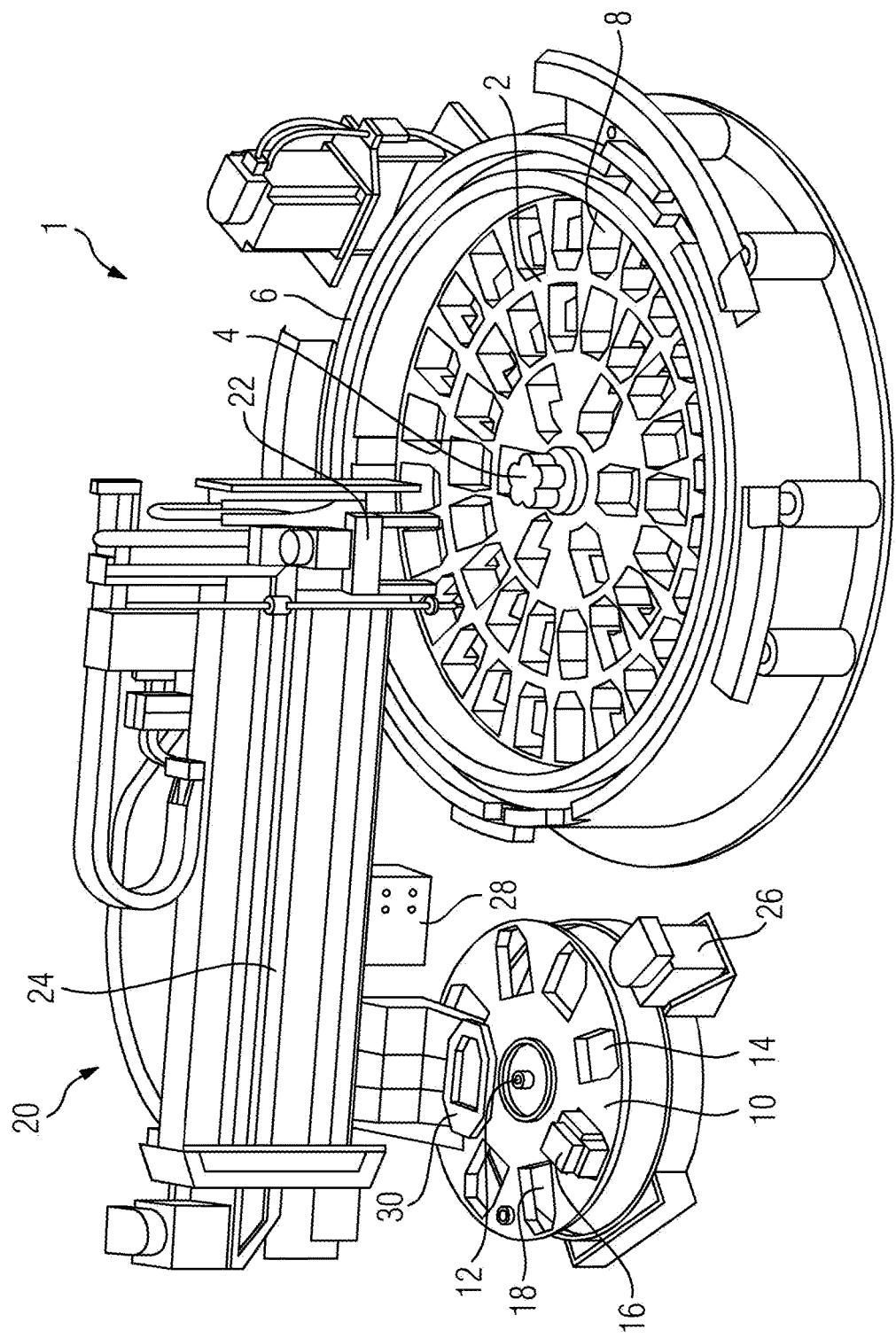

REAGENT STATION FOR AN AUTOMATED ANALYSIS DEVICE

The invention lies in the field of automated analysis devices for laboratory diagnostics and relates to a reagent station for an automated analysis device, comprising a first and a second reagent container storage and a transfer apparatus which transfers reagent containers between the first and the second reagent container storage. Furthermore, the invention relates to a method for loading an automated analysis device with reagent containers.

Numerous detection and analysis methods for determining physiological parameters in bodily fluid samples or in biological samples are these days carried out in an automated manner and in large numbers in automated analysis devices and also in so-called in-vitro diagnostic systems.

Current analysis devices are able to carry out a multiplicity of detection reactions and analyses with one sample. In order to be able to carry out a multiplicity of examinations in an automated manner, various apparatuses for spatial transfer of sample containers, reaction containers and reagent containers, such as e.g. transfer arms with gripping function, transport belts or rotatable transport wheels, as well as for transfer of liquids, such as e.g. pipetting apparatuses, are required. The device comprises a control unit which, by means of appropriate software, is able to plan and work off the work steps for the desired analyses in a largely independent manner.

Many of the measurement systems used in such automatically operating analysis devices are based on photometric measurement principles. These methods enable the qualitative and quantitative detection of analytes in liquid samples. Clinically relevant parameters, such as e.g. the concentration or activity of an analyte, are often determined by virtue of part of a bodily fluid of a patient, e.g. blood, plasma, serum or urine, being mixed in a reaction vessel with one or more test reagents, as a result of which a biochemical reaction, which brings about a measurable change in an optical or other physical property of the test mixture, is initiated.

The reagents required for the analyses are usually stored in appropriate reagent containers in a reagent container storage of a reagent station in the device. As a result of the many different types of analyses to be carried out, said reagent container storage typically comprises a multiplicity of receptacle positions for reagent containers and in many cases moreover comprises a cooling unit in order to ensure the shelf life of the reagents. The analysis device accesses the reagent container storage in an automated manner and, as required, takes the reagents necessary for the respective analysis by means of a transfer arm with a pipetting mechanism.

If one of the reagent containers has been used up or if it has exceeded its use-by date, it needs to be replaced. This must be carried out manually by a user. A problem arising here is that a manual replacement of reagent containers during the operation of the analysis device interrupts the operation of the device and reduces the test throughput because it is necessary to ensure by an interruption of the work processes in the device or at least by interruption of the access of the pipetting apparatus to the reagent containers that, firstly, the user is not injured by movable apparatuses of the device, such as e.g. pipetting apparatuses or rotating transport wheels, when accessing the reagent containers and that, secondly, no damage is caused to the movable apparatuses.

Until now, this problem was solved by virtue of completely interrupting the working off or else by restricting the access options of the user to the reagent container storage of a device in time.

Therefore, the prior art has disclosed analysis devices which provide for the loading of the reagent container storage in particular to be carried out by means of a second, separate reagent container storage. By way of example, to this end, a drawer is provided, into which the new reagent containers are successively inserted by the user. The new reagents are subsequently conveyed into the main reagent container in an automated manner by means of a transfer apparatus.

As a result of this, faster automated working off of the analyses is possible because the replacement of reagent containers can take place without interrupting the current operation. This is achieved by virtue of the direct manual access to the first reagent container storage, which is continuously accessed during operation of the analysis device by a pipetting apparatus for transferring reagent liquid, being completely prevented and the loading of the corresponding receptacle position with a new reagent container not taking place manually by a user but in an automated manner by means of an appropriate transfer apparatus.

It is now an object of the invention to provide a reagent station for an automated analysis device, which further increases the flexibility and enables, as far as possible, continual replacement of reagent containers by a user, without hindering device-internal work steps in the process.

According to the invention, this object is achieved by virtue of the receptacle positions of the second reagent container storage being arranged circularly and the second reagent container storage being rotatably mounted. To this end, the reagent container storage advantageously has a controllable rotation mechanism, such as e.g. a stepper motor.

As a result of the circular arrangement of the receptacle positions in conjunction with the rotatable design of the reagent container storage, the transfer apparatus can access each of the receptacle positions. This also applies and applies in particular if the transfer apparatus is designed in a particularly simple fashion for linear transport. As a result of this, it is possible that unloading and loading processes can occur simultaneously and the sequence of loaded and unloaded reagent containers can be planned in a fully flexible manner by a control unit and can be integrated in an optimized manner into the already planned analysis work steps. The manual access of the user is restricted to a receptacle position of the second reagent container storage, on which there is no continuous automated access by a pipetting apparatus during the analysis. Rather, the second reagent container storage is merely provided for loading, unloading and storing a plurality of reagent containers. The access to the second reagent container is therefore by hand on one side through a user access element, such as e.g. an access window, and automated on the other side by the transfer apparatus.

In order to load the device, a new reagent vessel is manually inserted into the second reagent container storage. As soon as the control unit establishes a suitable time which does not adversely affect the current analysis, a new reagent vessel is transferred from the second reagent container storage into the first reagent container storage by means of the transfer apparatus. Conversely, a used, no longer required reagent vessel is transferred from the first reagent container storage into the second reagent container storage by means of the transfer apparatus. In order to unload the device, the used reagent vessel is removed from the second reagent container storage by hand.

The receptacle positions of the first reagent storage are advantageously also arranged circularly. Here, a plurality of receptacle positions are particularly preferably arranged circularly in a plurality of concentric circles and the receptacle positions are arranged with radial symmetry. This allows access to all positions of the first reagent storage, even in the case of a linear design of the transfer system.

The circular arrangement of the receptacle positions in rotatably mounted reagent container storages enables access to all receptacle positions with, at the same time, a particularly simple design of the transfer apparatus, namely by virtue of the gripper mechanism of the transfer apparatus only having to move along a line which is directed to the center points of the reagent container storages. In this manner, the gripper mechanism merely needs to move along one dimension, while the respective receptacle position is moved under the gripper mechanism by rotation of the reagent container storages. Here, the receptacle positions are preferably arranged with radial symmetry.

The user access element allows access of a user to at least one receptacle position for a reagent container in the second reagent container storage of the reagent station. Reagent stations in automated analysis devices are usually surrounded by at least the housing of the analysis device in order to protect the in part highly sensitive reagents from unwanted temperature variations or light exposure. The user access element can be embodied in the form of an access window, i.e. in the form of an opening in the housing of the analysis device, which creates a connection between the interior of the device, in which the reagent station is arranged, and the device surroundings. The user access element is preferably a lockable access window, which can, for example, be locked by a flap or a sliding door.

The transfer apparatus serves for transferring reagent containers between the first and the second reagent container storage and vice versa. The transfer apparatus can have a different design, depending on the type of reagent containers to be transferred. The transfer apparatus preferably comprises a gripper mechanism, which is designed to lift the reagent containers from the receptacle positions or to place them therein. To this end, the gripper mechanism is preferably movably arranged on a guide rail which extends between the first and the second reagent container storage. The gripper mechanism can alternatively be on a robot arm. In a preferred embodiment, a gripper mechanism is equipped with a sensor which enables it to determine whether a receptacle position in a reagent container storage is occupied or unoccupied.

The reagent station furthermore preferably comprises a control unit configured such that, in a given position of the second reagent container storage, the transfer apparatus always accesses a different receptacle position for a reagent container than the user is able to by hand. This firstly enables a particularly high level of operational safety. Secondly, this enables a particularly effective replacement: the user inserts a reagent container in a receptacle position of the rotatable second reagent container storage and controls the rotation mechanism manually such that access is granted to a further receptacle position in the second reagent container storage. Here, a reagent container can again be inserted or removed, etc. As soon as the user has inserted all reagent containers, the transfer apparatus can operate in an automated manner and, depending on the prescription of the control unit, control the rotation mechanisms of the reagent container storages and the transfer apparatus for transferring the reagent containers from the second into the first reagent container storage.

In an advantageous embodiment, the control unit is configured such that, when a user accesses a receptacle position of the second reagent container storage, the transfer system has no access thereto. Although there is no automated access to the second reagent container storage by the pipetting mechanism for purposes of the analysis, there is however very much an automated access by the transfer apparatus. By configuring the control unit such that automated access by the transfer apparatus is prevented in the case of manual access by the user, the operational safety is increased since the user cannot be injured in the region of the second reagent container storage. To this end, the control unit is connected to a securing mechanism. By way of example, there can be securing by means of a photoelectric barrier in the region of the user access element, which interrupts the access of the transfer apparatus as soon as a user access is discovered. If the user access element is embodied as an access window, provision can be made for a lockable door or flap, with the transfer apparatus only being able to access a receptacle position in the locked state of the door or flap.

In a further advantageous embodiment, the reagent station comprises an identification mechanism for reagent containers. The identification mechanism can for example comprise a barcode reader, QR code reader or RFID reader, which reads out information printed onto the reagent vessels. Alternatively, the identification mechanism can comprise a digital camera which records a digital image of a reagent container and compares this to stored information in order to identify the different reagent containers.

The identification mechanism is preferably applied along the transfer path between the second and the first reagent container storage or on the transfer apparatus itself such that the type of the newly loaded reagent can already be established and stored during the transfer of a reagent container from the second into the first reagent container storage. As a result of this, the control unit already knows of the appropriate information during the transfer and the latter does not need to be established only after loading into the first reagent container storage. The advantage offered by this is, in particular, that the distances between the receptacle positions or from an edge of the reagent container storage to a receptacle position need not, neither in the first nor in the second reagent container storage, be selected to be so large that the information can still be read out here. As a result of this, more reagent containers can be housed on a reagent container storage with a given area and the device can have a more space-saving design.

In a further advantageous embodiment, the reagent station comprises a shaker mechanism for shaking the reagent containers. This is because some reagents require shaking up in order to avoid sedimentation or unmixing.

The shaker mechanism is preferably attached along the transfer path between the second and first reagent container storage or on the transfer apparatus itself such that a reagent container can be shaken during the transfer from the second into the first reagent container storage.

The shaker mechanism can be embodied in the form of a special receptacle position for a reagent container, into which a reagent container is transferred after it was removed from the second reagent container storage and the identification mechanism identified that this is a reagent to be shaken. By way of example, the special receptacle position for shaking can be embodied according to the principle of a vibrating table or in the form of a holder rotating by means of the head. Alternatively, the shaker mechanism can consist of a rotating eccentric mechanism according to the principle of a vortex mixer which, when a reagent container is brought into contact with the eccentric mechanism by the transfer apparatus, carries out a rotation movement and thus imparts mechanical vibrations on the reagent container.

In another embodiment the shaker mechanism can be integrated into the transfer apparatus. By way of example, to this end, the arm, to which the gripper mechanism for the reagent container is attached, can be embodied and controlled in such a way that the latter can carry out shaking movements during the transfer process.

A further subject of the present invention is an automated analysis device which comprises a reagent station according to the invention.

The invention furthermore relates to a method for loading an automated analysis device with at least one reagent container. The method according to the invention comprises the following method steps:

a) placing a reagent container into a receptacle position of a second reagent container storage,
b) rotating the second reagent container storage into a position such that a transfer apparatus can access the receptacle position,
c) removing the reagent container from the receptacle position by means of the transfer apparatus,
d) transferring the reagent container to a receptacle position of a first reagent container storage by means of the transfer apparatus and
e) placing the reagent container into the receptacle position of the first reagent container storage by means of the transfer apparatus.

The reagent container is preferably placed manually into a receptacle position of the second reagent container storage by a user.

In another preferred embodiment of the method, the reagent container passes an identification mechanism, for example a barcode scanner, a digital camera or an RFID reader, which captures information in respect of the identity of the reagent container or in respect of the container content, during the transfer to a receptacle position of the second reagent container storage.

In an in turn other preferred embodiment of the method, the reagent container is shaken before said reagent container is placed into the receptacle position of the second reagent container storage.

The advantages obtained by the invention consist of, in particular, the operational safety and the analysis throughput of an analysis device being significantly improved by using two independent, rotatable reagent container storages with circularly arranged receptacle positions which can be coupled by a linear transfer apparatus. Likewise, the user-friendliness is increased since the user can carry out the necessary loading and unloading of reagent containers at any time to suit him. The integrated shaking and identification functions do not reduce the throughput of the system.

The above-described arrangement is furthermore advantageous in that a plurality of reagent containers can be loaded by a user or in that there can be simultaneous loading and unloading. If the second reagent container storage were to have only one receptacle position, it would be possible to insert a reagent container without risk, but the user would then have to wait until the transfer apparatus, depending on the process plan of the control unit, has removed the reagent container again. This is avoided by a plurality of receptacle positions. A plurality of receptacle positions of the second reagent container storage can also be simultaneously accessible to the user by means of a user access element. Furthermore, provision can be made for manual access in each case to be granted to only one receptacle position at any given time.

The invention will be explained in more detail on the basis of a drawing.

DESCRIPTION OF THE FIGURES

FIG. 1 schematically shows the design of a reagent station 1 of an analysis device not depicted in any more detail. The reagent station 1 has a first reagent container storage 2, which the analysis device 1 accesses with a pipetting mechanism (not depicted in any more detail) during the analysis of a multiplicity of samples of bodily fluids carried out in an automated manner. For planning the work steps and entering the analyses desired by the user, the analysis device 1 has a control unit (not depicted in any more detail) which is designed as a personal computer.

The reagent container storage 2 has a circular design and is rotatably mounted about a shaft 4. The rotation is controlled by the control unit. The reagent container storage 2 is surrounded by a cooling unit 6 which ensures the shelf life of the reagents in the reagent container storage 2. The reagent containers themselves are not depicted; all that is shown are the receptacle positions 8 for the reagent vessels, which are arranged in concentric circles with three different radii about the shaft 4. Here, from the inside going out, the respective circles comprise six, eighteen and twenty-four receptacle positions 8, respectively, and so, overall, forty-eight receptacle positions 8 are present.

During routine operation, the reagent container storage 2 is inaccessible to the user. In order to load and unload the reagent containers, the reagent station 1 has a second reagent container storage 10, which is rotatably mounted about a shaft 12. The reagent container storage 10 comprises eight receptacle positions 14 for reagent vessels, which are arranged around the shaft 12 in a circular fashion. A reagent vessel 16 is depicted in a receptacle position 14. The user can access one of the receptacle positions 14 by means of a stationary, i.e. not co-rotating, access window not depicted in any more detail. The access window is arranged at the position 18 and has a lockable door.

The reagent station 1 furthermore comprises a transfer apparatus 20, comprising a gripper mechanism 22 which is embodied to lift the reagent vessels 16 from or inserts them into the receptacle positions 8, 14. The gripper mechanism is movably arranged on a guide rail 24 which extends substantially linearly between the shafts 4, 12. The reagent station 1 furthermore comprises a rotation mechanism 26 for automated rotation of the second reagent container storage 10. The gripper mechanism 22 is equipped with a sensor which permits the control unit to establish whether the respective receptacle position 8, 14 is occupied or unoccupied.

For the purposes of unloading one or more reagent containers 16 from the reagent container storage 2, for example due to expired use-by dates or due to use, the corresponding reagent container 16 is transferred from the reagent container storage 2 into the reagant container storage by means of the transfer apparatus 20. This process is carried out automatically by the control unit such that the work steps required for this can be integrated into the analysis procedure and do not lead to interruptions.

To this end, the reagent container storage 2 is initially rotated about the shaft 4 in such a way that the corresponding receptacle position 8 with the reagent container 16 to be replaced is arranged under the guide rail 24. The gripper mechanism 22 removes the reagent container 16 and transports it along the guide rail 24 to the reagent container storage 10. The reagent container storage 10 is rotated in such a way that an unoccupied receptacle position 14 lies under the guide rail 24 and the gripper mechanism 22 places the reagent container 16 into the unoccupied receptacle position 14. Subsequently, the reagent container 16 is transported to the position 18 by means of the rotation mechanism 26 such that it can be removed by the user through the access window. Here, the rotation mechanism 26 is designed such that it is inactive as soon as the door of the access window is opened.

The user can now insert a new reagent container 16 into a receptacle position 14. If further reagent containers 16 are to be inserted, the user can close the door of the access window and manually actuate the rotation mechanism 26 such that a further unoccupied receptacle position 14 is brought into the position 18. During this time, the analysis system can access the first reagent container storage 2 without hindrance. Once all desired reagent containers 16 have been inserted, the user starts the transfer. Now the control unit transfers the reagent containers into unoccupied receptacle positions 8 of the first reagent container storage by means of the transfer apparatus 20 in an automated manner, which reagent containers are integrated into the processes of the analysis in an optimum fashion.

To this end, the reagent container storage 10 is initially rotated about the shaft 12 in such a way that an appropriate receptacle position 14 with a newly inserted reagent container 16 is arranged under the guide rail 24. The gripper mechanism 22 removes the reagent container 16 and transports it along the guide rail 24 to the first reagent container storage 2. The reagent container storage 2 is rotated in such a way that an unoccupied receptacle position 8 lies under the guide rail 24 and the gripper mechanism 22 places the reagent vessel 16 into the unoccupied receptacle position 8. This process is repeated for all newly occupied receptacle positions 14 in the second reagent container storage 10, respectively controlled in an automated manner by the control mechanism, which optimizes the transfer in such a way that it does not adversely affect the analysis.

During the transfer, an identification mechanism 28 comprising a barcode reader, which identification mechanism is arranged in a stationary manner and in such a way that it can be reached by the transfer apparatus 20, reads out a barcode on the respective reagent container 16, said barcode containing information in respect of content and use-by date in particular. This information is stored in the control unit such that the control unit always has information in respect of the reagent containers inserted in each receptacle position 8 of the first reagent container storage 2.

The transfer apparatus 20 furthermore comprises a shaker mechanism 30 which can be reached by the gripper mechanism 22. A newly inserted reagent vessel can, prior to being put down in the first reagent container storage 2, be inserted and shaken up therein. Furthermore, the control unit can also, at regular intervals, arrange for reagent containers with reagents requiring this to be removed from the reagent container storage 2 by means of the transfer apparatus 20 and to be shaken up in the shaker mechanism 30. These steps can likewise be integrated into the procedure of the analysis in an optimized manner.

The invention claimed is:

1. A reagent station for an automated analysis device, comprising:

a first reagent container storage with a plurality of receptacle positions for reagent containers, the first reagent container storage having a first center point;

a second reagent container storage with a plurality of receptacle positions for reagent containers, wherein at least one receptacle position can be reached by a user using a user access element, the second reagent container storage having a second center point; and a transfer apparatus comprising a gripper mechanism configured to move in only first and second dimensions to transfer reagent containers between the first and the second reagent container storages, the transfer apparatus comprising a guide rail extending linearly between the first and the second center points, the gripper mechanism configured to lift and lower the reagent containers vertically in the first dimension into and out of at least one of the receptacle positions of each of the first and the second reagent container storages and move parallel to and along the guide rail in the second dimension;

wherein the receptacle positions of the second reagent container storage are arranged circularly and the second reagent container storage is rotatably mounted about the second center point and is nonconcentric with the first reagent container storage.

2. The reagent station as claimed in claim 1, further comprising a rotation mechanism for automated rotation of the second reagent container storage, wherein the rotation mechanism is inactive in response to the user using the user access element.

3. The reagent station as claimed in claim 1, which furthermore comprises an identification mechanism for reagent containers.

4. The reagent station as claimed in claim 1, which furthermore comprises a shaker mechanism for reagent containers.

5. The reagent station as claimed in claim 1, wherein the first reagent container storage is rotatably mounted.

6. The reagent station as claimed in claim 1, comprising a pipetting apparatus which accesses the first reagent container storage but not the second reagent container storage.

7. An automated analysis device comprising a reagent station as claimed in claim 1.

8. The reagent station as claimed in claim 1, wherein the first reagent container storage comprises a first shaft located at the first center point about which the first reagent container storage is rotatable.

9. The reagent station as claimed in claim 1, wherein the second reagent container storage comprises a second shaft located at the second center point about which the second reagent container storage is rotatable.

10. The reagent station as claimed in claim 1, comprising a control unit connected to a securing mechanism configured such that when a user accesses a receptacle position of the second reagent container storage as detected by the securing mechanism, the control unit prevents the transfer apparatus from accessing the second reagent container storage.

11. The reagent station as claimed in claim 10, wherein the securing mechanism comprises a photoelectric barrier or a lockable sliding door or flap in the region of the user access element.

12. The reagent station as claimed in claim 1, wherein the receptacle positions of the first reagent container storage are arranged circularly.

13. The reagent station as claimed in claim 12, wherein the receptacle positions of the first reagent container storage are arranged circularly in a plurality of concentric circles.

14. The reagent station as claimed in claim 13, wherein the receptacle positions of the first reagent container storage are arranged with radial symmetry.

15. The reagent station as claimed in claim 13, in which the transfer apparatus moves along a line which connects the center points of the circularly arranged receptacle positions.

16. A method for loading an automated analysis device with at least one reagent container, comprising the following successive method steps:

placing a reagent container into a receptacle position of a second reagent container storage, the second reagent container storage having a second center point, rotating the second reagent container storage about the second center point into a position such that a transfer apparatus can access the receptacle position, removing the reagent container from the receptacle position using the transfer apparatus, the transfer apparatus comprising a gripper mechanism configured to lift the reagent container vertically in a first dimension out of the receptacle position, transferring the reagent container along a guide rail of the transfer apparatus with the gripper mechanism to a receptacle position of a first reagent container storage via the transfer apparatus, the gripper mechanism configured to move parallel to and along the guide rail in a second dimension, the first reagent container storage having a first center point, and the guide rail extending linearly between the first and the second center points, and placing the reagent container into a receptacle position of the first reagent container storage via the transfer apparatus, the gripper mechanism configured to lower the reagent container vertically in the first dimension into the receptacle position of the first reagent container, wherein:

the first reagent container storage is nonconcentric with the second reagent container storage; and the gripper mechanism is configured to move in only the first and second dimensions.

17. The method as claimed in claim 16, wherein the placing the reagent container into a receptacle position of the second reagent container storage takes place manually by a user.

18. The method as claimed in claim 16, wherein the reagent container passes an identification mechanism which captures information in respect of the identity of the reagent container during the transfer to a receptacle position of the first reagent container storage.

19. The method as claimed in claim 16, wherein the reagent container is shaken before said reagent container is placed into the receptacle position of the first reagent container storage.

\* \* \* \* \*